(12) United States Patent
Pohlman et al.

(10) Patent No.: US 11,674,892 B2
(45) Date of Patent: Jun. 13, 2023

(54) DISCRETE SAMPLE INTRODUCTION MODULE (DSIM) FOR GAS ANALYSIS BY LASER ABSORPTION SPECTROSCOPY

(71) Applicant: UNITED STATES GEOLOGICAL SURVEY, Reston, VA (US)

(72) Inventors: John William Pohlman, East Falmouth, MA (US); Emile Marcel Bergeron, Falmouth, MA (US); Michael Andrew Casso, Falmouth, MA (US)

(73) Assignee: U.S. Geological Survey, Reston, VA (US)

( * ) Notice: Subject to any disclaimer, the term of this patent is extended or adjusted under 35 U.S.C. 154(b) by 67 days.

(21) Appl. No.: 17/020,343

(22) Filed: Sep. 14, 2020

(65) Prior Publication Data

US 2021/0310936 A1 Oct. 7, 2021

Related U.S. Application Data

(60) Provisional application No. 62/926,525, filed on Oct. 27, 2019.

(51) Int. Cl.
| | |
|---|---|
| *G01N 21/31* | (2006.01) |
| *G01F 15/00* | (2006.01) |
| *G01N 1/38* | (2006.01) |
| *G01N 1/24* | (2006.01) |
| *G01L 19/00* | (2006.01) |

(52) U.S. Cl.
CPC ............ *G01N 21/31* (2013.01); *G01F 15/00* (2013.01); *G01L 19/00* (2013.01); *G01N 1/24* (2013.01); *G01N 1/38* (2013.01); *G01N 2201/06113* (2013.01)

(58) Field of Classification Search
CPC ........... G01F 15/00; G01L 19/00; G01N 1/24; G01N 1/38; G01N 21/31; G01N 2201/06113; G01N 2033/4977; G01N 33/0014; G01N 33/0018; G01N 33/0067
USPC .................................................. 356/300–334
See application file for complete search history.

(56) References Cited

U.S. PATENT DOCUMENTS 4,010,100 A * 3/1977 Suslick .................. B01D 59/34
                                                                 95/82

OTHER PUBLICATIONS

Picarro, Inc.; Data Sheet—Liaison: Universal Interface for Bulk 13C Analysis [online]; retrieved from https://www.picarro.com/support/library/documents/liaisontm_universal_interface_datasheet; Picarro Document Library, 2010.
Picarro, Inc.; Data Sheet—A0314 (Small Sample Introduction Module 2) Datasheet [online]; retrieved from https://www.picarro.com/support/library/documents/a0314_small_sample_introduction_module_2_datasheet; 2018.

(Continued)

*Primary Examiner* — Tri T Ton
(74) *Attorney, Agent, or Firm* — James Mitchell

(57) ABSTRACT

A Discrete Sample Introduction Module (DSIM) apparatus includes an internal tubing system to receive into the DSIM apparatus a discrete gas sample having a received concentration. A plurality of valves selectively partitions the internal tubing system to form a plurality of loops corresponding to a plurality of loop volumes to contain the discrete gas sample. The plurality of loop volumes receives a carrier gas to dilute the discrete gas sample to a plurality of preselected dilutions. The DSIM apparatus circulates a given one of the plurality of preselected dilutions for analysis by a spectrometer coupled to the DSIM apparatus.

28 Claims, 12 Drawing Sheets

(56) References Cited

OTHER PUBLICATIONS

Wilson et al.; 'An intercomparison of oceanic methane and nitrous oxide measurements,' Biogeosciences vol. 15, issue 19, [online] retrieved from https://doi.org/10.5194/bg-15-5891-2018 ; Published Oct. 5, 2018.

* cited by examiner

DISCRETE SAMPLE INTRODUCTION MODULE (DSIM) FOR GAS ANALYSIS BY LASER ABSORPTION SPECTROSCOPY

CROSS-REFERENCE TO RELATED APPLICATIONS

This application claims the benefit of U.S. Provisional Application No. 62/926,525 entitled "Discrete Sample Introduction Module (DSIM) for Gas Analysis by Laser Absorption Spectroscopy," filed on Oct. 27, 2019, the contents of which is incorporated herein by reference in its entirety.

STATEMENT OF GOVERNMENT INTEREST

The invention described herein was made by employees of the United States Government and may be manufactured and used by or for the Government of the United States of America for governmental purposes without the payment of any royalties thereon or therefore.

FIELD OF INVENTION

This invention relates to the field of gas analyzers, such as Laser Absorption Spectroscopy (LAS), and to an apparatus that is operatively coupled with the spectroscope to analyze gas samples.

BACKGROUND

The U.S. Geological Survey is a bureau of the Department of Interior which has the sole mission of acquiring objective scientific data about the Earth. Scientists at the USGS Woods Hole Coastal & Marine Science Center located in Woods Hole Massachusetts (USA) have made advancements in the field of trace gas analysis and Laser Absorption Spectroscopy (LAS) which enable scientists to forensically identify the source or producer of greenhouse and other gases of environmental and eco concern. Scientists are also able to definitively identify the biological or geological processes which created a gas by measuring the isotopic signature of gases.

Isotopic signature data is sometimes analogized to DNA or fingerprints. Isotopes are variations of an element that have the same number of protons but a different number of neutrons in the nucleus. Isotopes have all characteristics of the element but are distinguishable by their atomic weight. Elements present in compounds, such as carbon, hydrogen, nitrogen and oxygen have highly distinctive isotopic ratios which identify conditions and biochemical processes under which the gas was produced.

Scientists obtain isotopic data using Laser Absorption Spectroscopy (LAS) methods to identify the concentration of specific gas isotopes by observing how light of specific wavelengths is absorbed.

Laser spectrometers known in the art can accurately measure trace gas concentrations and, in some cases, their isotopic composition through known methods. However, testing requires samples be delivered with gas passing through a spectrometer under flow-through methods, which obtain continuous readings from ambient air flow to detect minute concentrations of gases. This is done without use of controlled volumes.

In certain cases, scientists require the ability to obtain instant, accurate measurements of a gas concentrations of all ranges and isotopic data onsite to determine if and where a gas source may be emanating.

Scientists are currently able to adapt a laser spectroscope such as a cavity ring-down spectrometer (CRDS) with a device known in the art as a Small Sample Introduction Module for discrete sample analysis for trace gas.

The CRDS and the SSIM are manufactured by Picarro, Inc. When coupled with the spectroscope, the SSIM forms a pathway through which the discrete sample is loaded into an evacuated chamber before it is passed through the CRDS to obtain readings for a 4-8-minute interval. Gas that passes through the analyzer is exhausted from the system. It is known in the art that some discrete samples may have high concentrations of analytes that exceed the analytical range of a LAS spectroscope, resulting inaccurate measurements of the gas concentrations.

In particular, gas samples obtained from near or below the earth's surface or ocean floor frequently have analyte concentration levels which exceed the analytical range of a LAS. This inability to analyze high concentration samples limits concentration and isotopic data available to evaluate the content and origin of natural gas, and to predict the quantity and type of gases that may be introduced into the environment during gas leaks and production.

As a result, there is an unmet need for precise, reliable gas analyzers, equipment and methods that can be used to determine sources of gases and their concentrations ranging from parts per million to 100% analyte.

SUMMARY OF THE INVENTION

The invention is a Discrete Sample Introduction Module (DSIM) apparatus that is operatively coupled with a laser spectroscope forming a closed system capable of performing Laser Absorption Spectroscopy (LAS) on discrete gas samples having concentration ranges of low parts per million to 100% of analyte. The closed system is formed by operatively coupling the DSIM and spectroscope. The gas sample to be tested is introduced to the DSIM and mixed with a zero gas at a controlled, fixed volume resulting in dilution from greater than 0 to 99.9%. The dilution sample gas goes through the spectroscope, also referred to as gas analyzer. The controlled, quantitative dilution performed by the DSIM enables calculation of accurate concentration and isotopic data for samples having analyte concentration of all levels. This could not otherwise be achieved, as the undiluted sample concentration would exceed the uppermost range of the gas analyzer instrument absent the DSIM.

In embodiments, the DSIM apparatus may be operatively coupled to spectroscopes that employ various alternative Laser Absorption Spectroscopy techniques including but not limited to cavity ring-down spectroscopy (CRDS), off-axis integrated cavity output spectroscopy (ICOS), tunable diode laser spectroscopy (TDLAS) and optical Feedback—Cavity Enhanced Absorption Spectroscopy (OF-CEAS) and Fourier Transform Infrared Spectroscopy (FTIR).

The DSIM includes an internal tubing system with a total fixed internal volume that can be selectively configured and partitioned using electrically actuated valves and other mechanical components to form one or more alternative paths for the conveyance of sample gas within a DSIM. Alternative paths are configured and selected depending on the operation being performed and whether sample dilution is required.

Operations performed by the DSIM include but are not limited to discrete sample gas analysis without dilution, sample dilution prior to analysis, step down dilution during analysis, and purging of analyte artifacts from the system before and after dilution.

The DSIM apparatus includes two or more alternative sample inlets for loading a discrete gas sample into the closed system.

The DSIM includes at least one Non-dilution Sample inlet (referred to as the System Load Inlet) which receives discrete gas samples that recirculate within the closed system for analysis without dilution. This inlet is referred to as the System Load Inlet because the volume of entire fixed internal tubing system is loaded with the sample gas through this inlet. By not diluting the sample, the measurement of the sample is the actual sample concentration and maximum instrument sensitivity is achieved.

The DSIM further includes at least one Dilution Sample Inlet, referred to as the Loop Load Inlet. This inlet is referred to as the Loop Load Inlet because when a sample is loaded for dilution, the sample gas is confined within a Sample Loop structure having a fixed internal volume comprising a portion of the fixed volume of the internal tubing system. The fixed internal volume of the sample precisely controls the volume of sample gas loaded for dilution. Only the Sample Loop, rather than the entire internal tubing system, is loaded with the sample gas. The Sample Loop is operatively coupled with mechanical components that are controlled to partition and isolate a precisely quantified volume of sample gas from the rest of the internal tubing system. The remaining portion of the internal tubing system is supplied with a zero gas such as a carrier gas that is delivered to the LAS during the loop loading process.

The isolated Sample Loop (Loop A and B) is filled with a sample gas. Valves (V1-V5), such as multi-port rotary valves, are independently opened and closed to control flow of gas to release the sample gas from the selected loop into the closed system loop analysis path to mix with the zero-gas forming a diluted sample gas. By recirculating the diluted gas through the closed system loop, the gas is uniformly mixed placing the concentration of the gas sample or analyte within the sensitivity range of the gas analyzer to produce accurate measurements.

Sample Loops that pass gas samples to a gas analyzer, may be external and/or internal using tubing bent to fit dimensions within the DSIM, removable and/or fixed with known connectors. The volume of the DSIM closed system loop can be expanded using additional tubing and/or any known reservoirs or structures. In an embodiment, Expansion Volume Cylinder 50 may be used to expand the closed loop system to a volume of 300 ml. Each Sample Loop has a preselected, fixed interior volume which controls the volume of sample gas to enter the closed system. In an embodiment, the DSIM enables controlled dilution by no dilution factor, a dilution factor of 100:1, a dilution factor of 800:1, and a dilution factor of 1500:1, and continuous ranges therebetween.

In an embodiment, the DSIM is used to provide a continuous operational range for methane concentrations using DSIM sample introduction methods associated with overlap of a plurality of dilution factors. This enables the DSIM to achieve a full spectrum of known diluted concentrations for methane. For example, the system analysis operational mode provides an operational range of concentrations from approximately 100 parts per billion (ppb) to 1000 parts per million (ppm). The system analysis operational mode overlaps with the Loop B analysis operational mode. The Loop B analysis operational mode provides an operational range of concentrations from approximately 1000 ppm to 10%. The Loop B analysis operational mode overlaps with the Loop A analysis operational mode. The Loop A analysis operational mode provides an operational range of concentrations from approximately 3000 ppm to 30%. The Loop A analysis operational mode overlaps with the Loop A analysis operational mode with Expansion. The Loop A analysis operational mode with Expansion provides an operational range of concentrations from approximately 30% to 100%. Accordingly, the combined range of the various operational modes enables the DSIM to reach from a diluted sample at 100 ppb, to a 100% non-diluted sample.

The DSIM contains various loops to admit multiple preselected volumes of sample gas into the closed analysis system. The selection in loop volume changes the sample gas dilution. The range or sensitivity, according to which the gas analyzer is able to accurately measure concentrations and isotopes of a gas, is based on the source of the gas. Where the targeted gas is, for example, methane, carbon dioxide, or other gas, the analyzer's sensitivity range is different for each targeted gas. The loop selected in the DSIM is based on the total volume needed to dilute the gas to a level within a sensitivity of the connected gas analyzer. The DSIM allows for selection or combination of various different internal loops with corresponding respective different volumes. Furthermore, the DSIM can interface with additional, e.g., external loops to further adjust the total volume corresponding to the various selected loops. More specifically, for methane gas, an external loop having a 1 ml volume can be used, in conjunction with the volume of an internal loop, to create a total volume appropriate to dilute the methane gas and bring the diluted gas within range of the spectrometer for analysis. For carbon dioxide, an external loop of 5 ml volume can be used to dilute the carbon dioxide gas, to a total volume appropriate for analysis. Such example external loop volumes are consistent with establishing a range of dilution appropriate for the spectrometer 10 to analyze the gas. The DSIM includes different loops, internal and external, to create total volumes appropriate for a given gas, as well as for a given type of spectrometer. More specifically, the DSIM can determine which external loop volume, and selection of internal loop(s), is appropriate for creating a total volume to dilute a given sample gas to a level consistent with analysis by a given type of spectrometer interfaced with the DSIM.

In another embodiment, the DSIM is configured to request input on the type of gas to be analyzed, and its expected concentration range. For example, a computing device including logic provides a visual menu display including drop-down selections for the user to indicate which sample gases are to be analyzed. The DSIM is configured to then, responsive to receiving the input, provide information on what size or type of external loop to use appropriate for analyzing that type of gas and concentration range. For example, if the input received indicates methane gas, the DSIM informs the user to connect the 1 ml external loop. If the input indicates carbon dioxide gas, the DSIM informs the user to connect the 5 ml external loop.

The DSIM further includes a gas drying system for removing water that may have been present in the discrete gas sample. Water vapor is removed from the sample as it circulates within the internal tubing system. Water removal increases instrument performance by preventing water from interfering with the analyte absorption spectrum.

The DSIM may contain a reservoir of carrier gas with electrically actuated inlet and outlet structures that adds additional volume to the closed system which precisely and additionally dilutes a sample when use of a designated sample loop does not provide enough dilution.

The DSIM, in embodiments, can further include a Bypass Line for diverting a portion of the gas away from the analyzer during dilution and mixing of the carrier gas and sample gas, to expedite the rate at which the gases are circulated and mixed. This is a result of a pump (not shown) internal or external to the gas analyzer, pulling gas in the analyzer at a rate smaller than pump (P1) along the Bypass line. Use of pumps P1-P3 facilitates circulation of the gas within the system and increases the mixture of targeted and/or gas sample throughout the closed loop system. Flow meters, M1-M3, are placed within the DSIM 100, to verify pump performance, while known Pressure Sensors (R1-R2) may be used to monitor DSIM pressure to ensure the device is functioning properly. In an embodiment, the use of the Bypass Line reduces the time of mixing within the closed system from more than 20 minutes to less than 5 minutes. Other embodiments make use of one or more bypass lines to reduce the time of mixing within the closed system even further.

The DSIM is a single, field portable device capable of performing sample dilution to increase the upward range of concentrations an analyzer can measure by as much as three orders of magnitude (>1000×), while also being able to accurately analyze samples without dilution. Data from diluted samples is highly precise (generally <1% relative standard deviation (rsd)), isotopically accurate, and is independent of the gas constituent being measured. Sample dilution is achieved by limiting the volume of sample introduced into a recirculating analytical system, increasing the volume of the analytical system to accommodate additional dilution gas, or some combination of both.

TERMS OF ART

As used herein, the term "Internal Tubing System" means tubing within a DSIM apparatus which has a total fixed internal volume that can be selectively partitioned by the use of valves and other mechanical components to form one or more alternative paths for the conveyance of gas within a DSIM, including but not limited to a discrete sample gas and gases used for dilution and instrument calibration.

As used herein, the term "Sample Loop" means a partitioned area within the internal tubing system of a DSIM which has a fixed internal volume which may be used to isolate and contain sample gas to control the volume of gases introduced into the closed system formed when a spectrometer and DSIM are operatively coupled. A sample loop may have an internal or external loop structure that is coupled with the internal tubing system or an exchangeable external sample loop for lesser dilution.

As used herein, the term "Path" means the area within the internal tubing system through which a gas introduced into a DSIM is contained, conveyed, recirculated, mixed, analyzed and/or discharged.

As used herein, the term, "Bypass line" or "Bypass assembly" refers to any physical structure which diverts a portion of a sample gas from the sensing components of a gas analyzer to a pathway with enhanced mass flow for mixing and dilution of a sample with carrier gas during analysis.

As used herein, the term, "Dilution Factor" means a standard flow-thru concentration divided by a concentration measured by indicated analysis mode. Dilution Factor (DF) also may be expressed as a percentage dilution, where the percentage dilution is equal to 100%−((1/DF)*100%). For example, a dilution factor of 227 may be expressed as a 99.56% dilution; a dilution factor of 88.2 may be expressed as a 98.87% dilution; and a dilution factor of 1423.1 may be expressed as a 99.93% dilution.

As used herein, the term, "Discrete Sample" means a sample taken from an area under study (i.e., the test matrix).

As used herein, the term "dryer tube" or "dryer" means a tube or other structure comprised of a material adapted for drying a gas, including but not limited to a tube comprised of sulfonated tetrafluoroethylene based fluoropolymer-copolymer tube (such as the a NAFION® dryer tube manufactured by Perma Pure, LLC.)

As used herein, the term "Laser Absorption Spectroscopy (LAS)" means optical spectroscopic methods including but not limited to cavity ring-down spectroscopy (CRDS), off-axis integrated cavity output spectroscopy (ICOS), tunable diode laser spectroscopy (TDLAS), Optical Feedback-Cavity Enhanced Absorption Spectroscopy (OF-CEAS), and Fourier Transform Infrared Spectroscopy (FTIR).

As used herein, the term "load" or "loading" means the process of introducing a sample into the closed system formed when a DSIM and spectroscope are operatively coupled.

As used herein, the term "non-destructive" refers to a system which does not alter a sample during testing.

As used herein, the term "zero gas" refers to a gas lacking an analyte of interest and which may function as a carrier gas or be used during a purging operation.

As used herein, the term "standard gas" means a gas stored in a pressurized cylinder that contains a gas or gases with a known concentration and/or isotopic composition. In various embodiments, standard gas is used for calibrating an instrument and monitoring instrument stability during operation.

As used herein, the term "vent" refers to any port or physical structure for a gas to exit the closed system formed by coupling a DSIM and spectrometer.

As used herein, the term "Sample Inlet" refers to a port, aperture or connective structure for introducing samples into a closed system formed when a DSIM and spectroscope are operatively coupled.

As used herein, the term "System Load Inlet" refers to an inlet port for loading samples that are measured directly without dilution.

As used herein, the term "Loop Load Inlet" refers to an inlet port for samples that require dilution prior to measurement by a gas analyzer.

As used herein, the term "spectrometer" means a non-destructive, flow-through, low-leak instrument that measures gas concentrations and/or gas isotope ratios using an optical absorption technique. Spectrometer is also referred to herein as gas analyzer.

As used herein, the term "stepdown dilution" is a method of reducing analyte concentration during an analysis, and which may be performed as brief and repeated activations of the system purge mode.

DETAILED DESCRIPTION OF THE DRAWINGS

Figure 1:
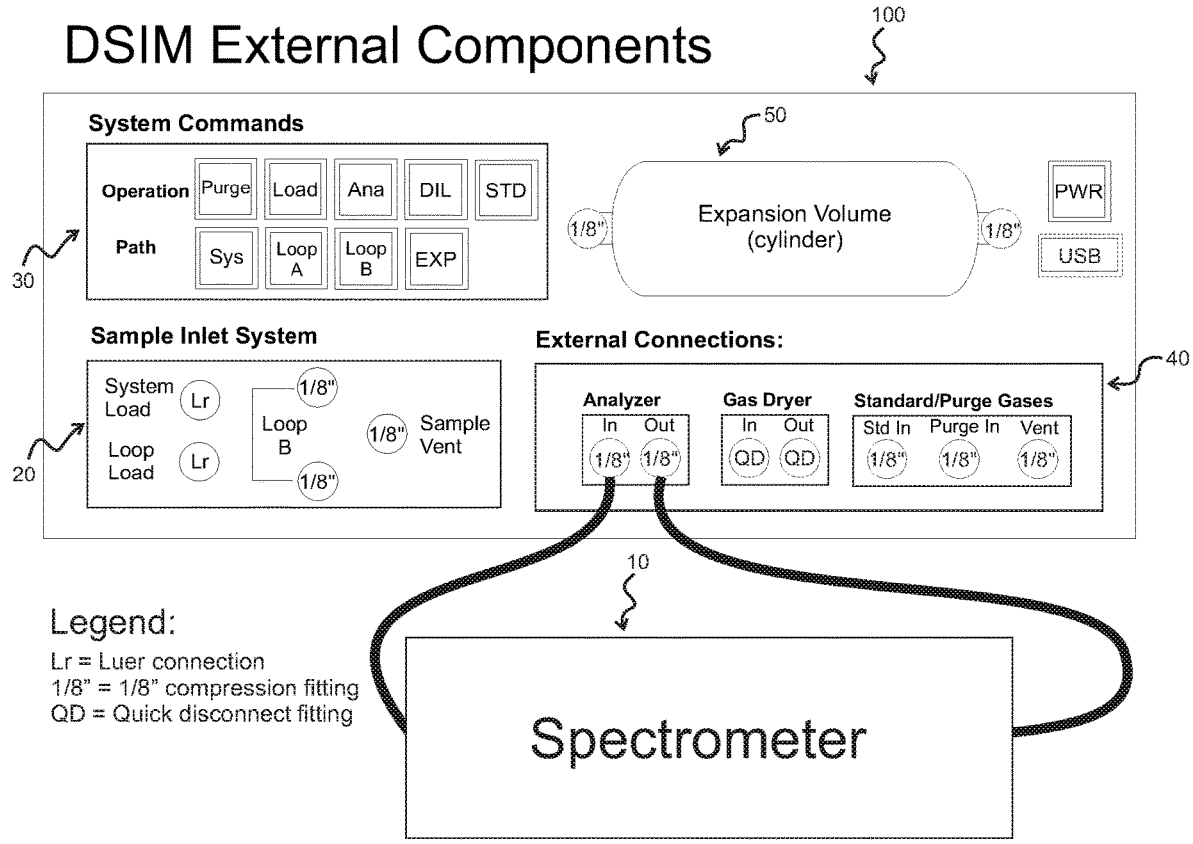
FIG. 1 illustrates a front view of an exemplary DSIM Apparatus operatively coupled to a LAS spectroscope.

FIG. 1 illustrates a front view of an exemplary DSIM Apparatus 100 operatively coupled to a LAS spectroscope 10.

In the exemplary embodiment shown, the DSIM 100 is a compact, field-portable apparatus that is operatively coupled with a LAS Spectrometer to form a closed system through which a sample may be nondestructively recirculated to enable Spectrometer 10 to obtain continuous readings required to perform LAS testing on a discrete sample in a laboratory or field setting.

The external components illustrated in FIG. 1 include buttons that activate system command operations and configure internal gas flow paths, and a USB port for external computer control of the system commands. DSIM 100 includes ports for entering samples into and venting gas from the sample inlet system. The sample inlet system also includes the external component of the exchangeable sample Loop B, which allows the user to control the loop volume and, hence, the magnitude of sample dilution.

In in the exemplary embodiment shown, DSIM 100 includes Sample Inlet Panel 20, System Command Panel 30, External Connection Panel 40 and Expansion Volume Cylinder 50.

Prior to introducing the sample gas from a discrete gas sample into the closed recirculating system formed by DSIM 100, a Purge function is initiated using the Purge button and the button that defines the flow path of the upcoming sample on System Command Panel 30 (e.g., Sys, Loop A, Loop B, EXP). During the Purge function a zero gas is pushed through the entire system to expel sample gas artifacts from the system through the DSIM Purge vents. The system purge is stopped when the gas analyzer no longer measures readings for the analyte, resulting in the system being purged. At this point valve V3 is positioned to trap the zero gas within the closed system.

As illustrated in FIG. 1, System Command Panel 30 includes buttons which activate commands that control system operations and determine active flow paths. In various embodiments these commands may also be activated by an external computer through the USB port or alternate port to control a micro-controller and/or other voltage regulating electronics. The System Commands on the front panel are used to achieve DSIM system configurations. Standard gas (Std In) and Purge gas (Purge In) flow directly through the closed system and exhaust from the Vent port. Suitable connection types include Ana=Analyze; DIL=Dilute; STD=Standard. The System Command settings are used to activate the DSIM operational modes.

In the exemplary embodiment shown, Sample Inlet Panel 20 includes two alternative Inlet Ports for introducing samples into DSIM. The System Load Port is used for applications which do not require dilution. The Loop Load Port is used for applications requiring dilution of high concentration samples.

In the exemplary embodiment shown, fittings for Loop B allow the user to connect external sample loops of differing volumes to achieve a range of sample dilution ratios.

As illustrated in FIG. 1, a sample vent allows gas, displaced during sample loading, to exhaust.

Also visible in FIG. 1 is an Expansion Volume Component which includes a reservoir of dilution gas and an interior volume which is operatively coupled with the internal volume of the internal tubing system of the DSIM. Where a too high gas sample concentration is put into smaller loop (for example Loop A), adding more zero gas to the closed system creates greater dilution. The expansion volume is an optionally utilized component of the analytical path.

External Connection Panel 40 includes connections for additional external components. For example, an inlet (In) and outlet (Out) are provided for sample gas recirculating between the DSIM and the gas analyzer (spectrometer 10 shown). An inlet (In) and outlet (Out) are provided for drying gas recirculating between an external desiccant (see FIG. 2) and the DSIM-internal NAFION® dryer. Standard gas (Std In) and Purge gas (Purge In) flow directly through the analytical system and exhaust from the Vent port. Suitable connection types are indicated in the legend. The System Command Panel 30 includes various abbreviations, including Ana=Analyze; DIL=Dilute; STD=Standard; Sys=System; EXP=Expansion.

DSIM 100 further incudes drying gas ports for recirculating air between the external desiccant (FIG. 2) and the DSIM-internal dryer comprised of sulfonated tetrafluoroethylene-based fluoropolymer-copolymer tube (such as the NAFION® dryer tube manufactured by Perma Pure, LLC).

Each of nine (9) buttons on the front panel of DSIM 100 activate a configuration change. The operational commands change the active function (i.e., what the DSIM 100 does) and the path commands change the path that gases follow within the selected function. Thus, with these nine commands, there are 17 possible operational modes. Various command combinations define the operational modes. Operational modes that include Loop A include with or without the Expansion Volume. Technically, the Expansion Volume can be used in any mode, but it is mostly useful when used with Loop A as it provides maximum system dilution. In an embodiment, the purge operational mode can be selected for the System (SYS, see FIG. 3), Loop A (Expansion EXP optional), or Loop B (see FIG. 3). Such corresponding figures and those below illustrate diagrams of operational modes. The load operational mode can be selected for the System (SYS, see FIG. 4), Loop A (Expansion EXP optional, see FIG. 5), or Loop B (see FIG. 6). The Analysis operational mode (Analyze (Ana)) can be selected for the System (SYS, see FIG. 7), Loop A (Expansion EXP optional, see FIG. 8), or Loop B (see FIG. 9). The stepdown operational mode (Analyze (Ana) and Dilute (DIL)) can be selected for the System (SYS, see FIG. 11), Loop A (Expansion EXP optional), or Loop B (see FIG. 11). The Standard Analysis operational mode also can be selected (Standard (STD), see FIG. 10).

In the exemplary embodiment shown in FIG. 1, the DSIM controller is actuated using front panel switches to configure the different operational modes of DSIM 100 as set forth above. Alternatively, DSIM operational modes are configured using a microcontroller configured with open source software known in the art such as ARDUINO®. In other embodiments, DSIM operational modes may be configured using a field programmable gate array (FPGA) that controls an interface board with multiple electro-mechanical relays, air pump speed controllers and voltage regulation. As the numerous operational modes can involve one or more valves and pumps to actuate based on the selected configuration, panel switches are wired to the digital inputs of the microcontroller and the digital outputs are wired to the interface board. Code is embedded in the internal microprocessor or alternatively provided by an external computer with systems engineering software (e.g., LABVIEW®) that enables the proper output bits to toggle relays for the shut-off valves and select the proper multivalve port and air pump based on the selected configuration.

Figure 2:
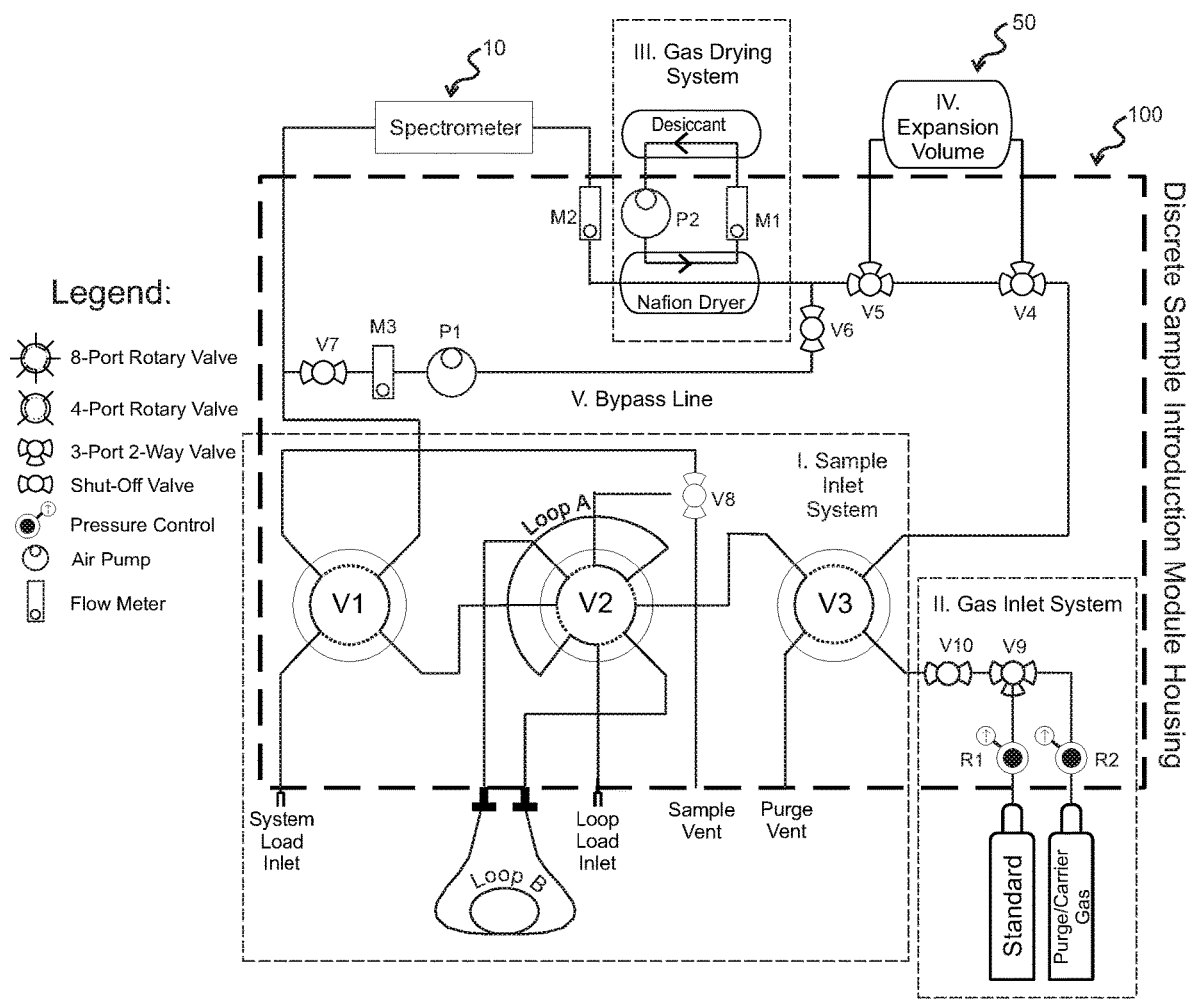
FIG. 2 is a schematic illustration of DSIM system components and their interoperability.

FIG. 2 is a schematic illustration of DSIM system components and their interoperability. In the exemplary embodiment shown, DSIM 100 is comprised of a Sample Inlet System (I) for the introduction of samples, a gas inlet system (II) for standard (calibration) analysis and system purging, a gas drying system (III) for removing water from the internal tubing path (also referred to as analytical path), an expansion volume component (IV) for additional sample dilution (when required to increase the fixed internal volume of the internal tubing system and amount of carrier gas present), and a Bypass Line (V) for expediting the mixing of gas samples and carrier gas within the internal tubing system. The DSIM 100 interfaces with a gas analyzer, also referred to as spectrometer 10, that measures gas concentrations by laser absorption spectroscopy.

In various embodiments, the DSIM 100 is coupled with a laser absorption spectrometer or other gas analyzer to perform highly accurate testing of discrete samples obtained from a remote testing location (matrix).

Prior to introduction of a discrete gas sample, the DSIM 100 system is purged with a zero air (or other suitable purging gas) to remove all traces of the analyte measured by the analyzer.

Where the sample gas is low concentration or a trace gas, it is loaded for processing without dilution using the System Load Inlet port and System Load Mode. The sample gas fills up the complete system. The gas analyzer takes continuous readings until its readings are leveled off.

Alternatively, a discrete gas sample believed to be higher concentration than the range of the analyzer is added for processing with dilution using a Loop Capture mode.

In various embodiments, the DSIM 100 may perform dilution in Sample Loop Inject mode with using an internal sampling loop for high dilution applications or an exchangeable external sample loop for lesser dilution.

Various components (e.g., paths or operational modes) of the DSIM 100 may be selected by a user (e.g., using System Command Panel 30) to cause the DSIM 100 to convey a discrete sample along alternate processing paths, which the DSIM 100 uses depending on the concentration level of an analyte with a sample.

In one exemplary embodiment, DSIM 100 includes an option for three levels of dilution. In this exemplary embodiment, high concentration samples (up to 100% of analyte) may be diluted by more than 99.9% using a fixed sample loop and the Expansion Volume. For low concentration samples where no sample dilution is desired, the entire (<100 ml) analytical system is loaded with the sample prior closure of the loop.

For intermediate concentration gases, an external sample loop is available and may be replaced with a volume suitable for a sample type and analyzer range (as may be determined by the user or the DSIM 100).

As the sample gas is conveyed within the system of internal tubing, the gas is preferably purified with a dryer, such as a sulfonated tetrafluoroethylene based fluoropolymer-copolymer tube such as the a NAFION® dryer tube manufactured by Perma Pure LLC. The dryer reduces water content. The drying gas for the NAFION® dryer is either room air pumped across a desiccant or a dry-gas cylinder, as determined by the user.

The dry-gas cylinder is filled with a "zero-air," consisting of 80% nitrogen and 20% oxygen or other gas lacking the analyte of interest, which is compatible with the spectroscope. The zero air is also used to purge the analytical loop after the analysis of each sample, and to prepare the loop for the introduction of the following sample. The system is equipped with an inlet for introducing a reference gas of known concentration and isotopic composition for periodic system calibration.

Figure 3A:
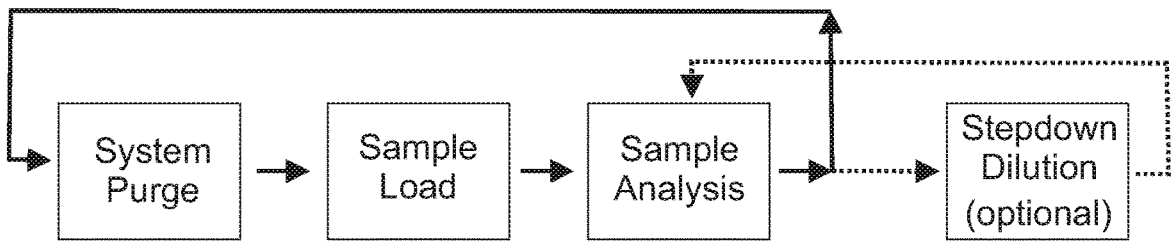
FIG. 3A illustrates the purge-load-analyze cycle common to processing both diluted and undiluted samples.

FIG. 3A illustrates the purge-load-analyze cycle common to processing both diluted and undiluted discrete gas samples.

Sample analysis is initiated with a system purge to flush analyte, e.g., as left over from a previous analysis, from the system.

System Purge is followed by a separate Sample Load and Sample Analysis operation (upper path, solid line) or a Standard Analysis that loads and analyzes the standard gas (lower path, solid line). Where a Standard is used, a gas with a known concentration that fits within the analytical range of the analyzer is introduced into the standard inlet ("Std In" shown in FIG. 1) to ascertain if the analyzer is functional.

Where dilution is necessary due to too high concentration, a standard having a known concentration that exceeds the analytical range of the spectrometer is placed in DSIM fixed loops. Due to the set volume of either Loop A, B and the remaining closed system, the gas analyzer's reading after dilution with such a gas sample provides a reference parts per million of the concentration. The process is duplicated with the same type of gas having an unknown concentration. Where the same type of gas is being examined, the results are compared. In an embodiment, Loop A has a set volume of 0.1 ml, while the entire internal DSIM closed loop system is 70 ml. In embodiments where the volumes are mechanically set, eliminating inconsistent dilution mixtures, the analyzer's result of the two gases (known and unknown sample concentrations) may be calculated with accuracy using ratios of the two gas results. Due to the control of the volumes, dilution error is eliminated, and resultant dilutions are known with accuracy and precision.

If the sample concentration of either a diluted or undiluted sample exceeds the gas analyzer's operational range, or if the user would like to determine the limit of detection for the spectrometer by progressively diluting to the sample to below the analyzer's limit of detection, an optional stepdown dilution process may be performed after the analysis step (dashed line) as described in the description of FIG. 12. The stepdown dilution process performed by the DSIM ensures the most precision and least amount of uncertainty in measurements, compared to other approaches that use arbitrary dilution or that dilute without using the stepdown approaches described herein.

Figure 3B:
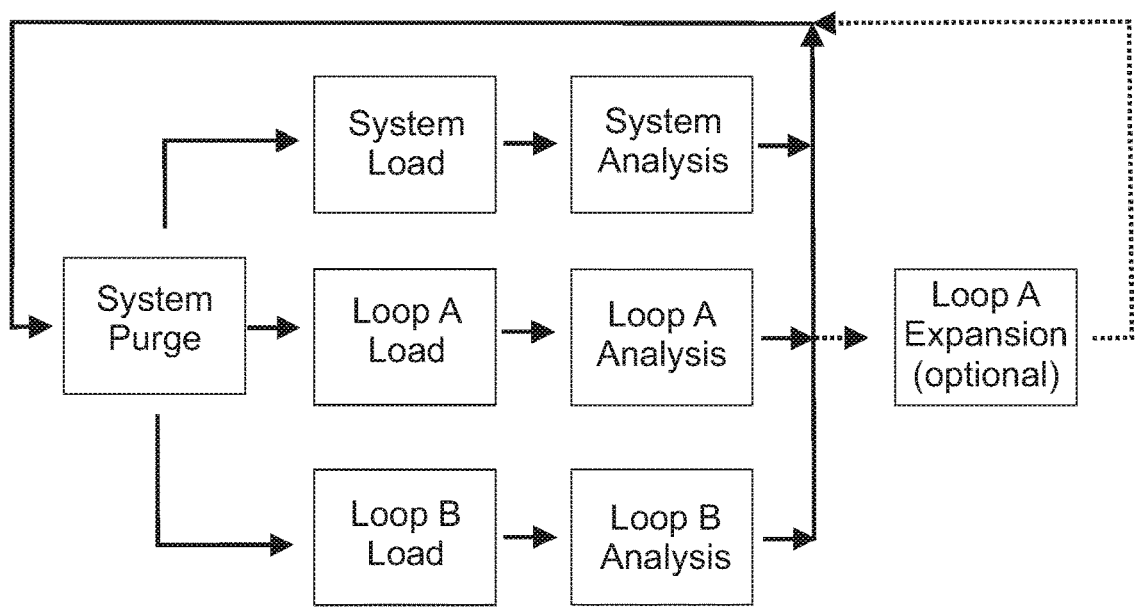
FIG. 3B Illustrates the processing sequence for three different gas sample concentrations which includes diluted and undiluted samples.

FIG. 3B illustrates the processing sequence for three different concentrations of discrete gas samples. As FIG. 3B illustrates, following System Purge, samples that do not require dilution are introduced to the DSIM during System Load and measured during System Analysis (top path). To dilute samples exceeding the gas analyzer's operational range, small sample volumes are introduced through a fixed low-volume (~0.1 ml) Loop A or an exchangeable larger-volume (1-10 ml) Loop B followed by Loop A Analysis and Loop B Analysis. For cases where greater sample dilution within Loop A is required (e.g., analyte concentration >50%), Loop A Expansion is enabled (dashed line). For both flowcharts, details about the configuration(s) for each step in the flowchart are provided in the referenced figure numbers.

Figure 4:
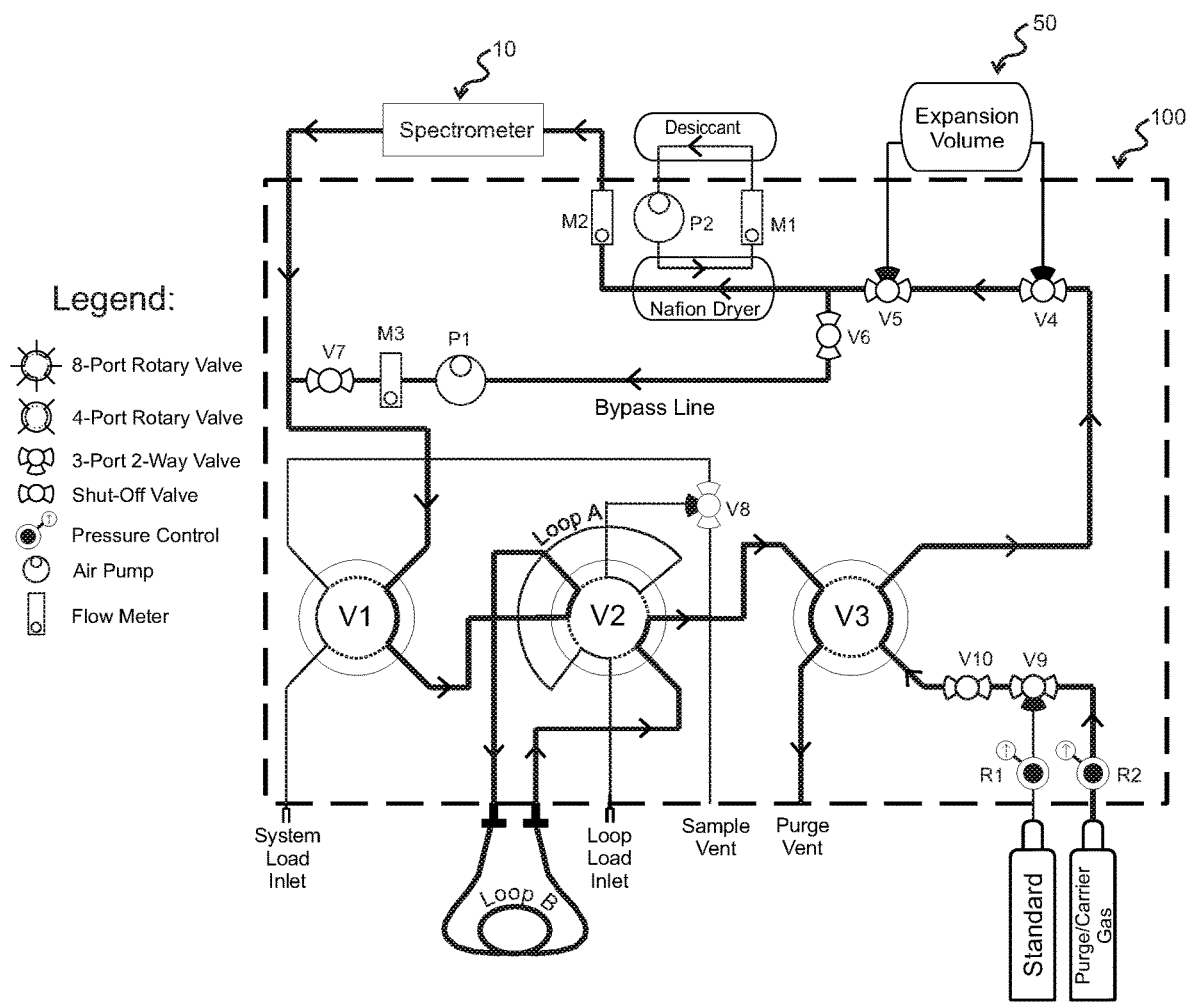
FIG. 4 illustrates an exemplary DSIM system configuration for a Purge operation.

FIG. 4 illustrates an exemplary DSIM system configuration for a Purge operation. Before analysis of each sample, Purge Gas flushes the previous sample from the analytical path for the upcoming sample. The purge path is depicted by the thick, solid arrowed line. In this configuration Loop B is being purged. Alternate configurations (not pictured) purge Loop A and the Expansion Volume, based on the valves being configured to direct purge gas through Loop A and/or the expansion volume areas.

Figure 5:
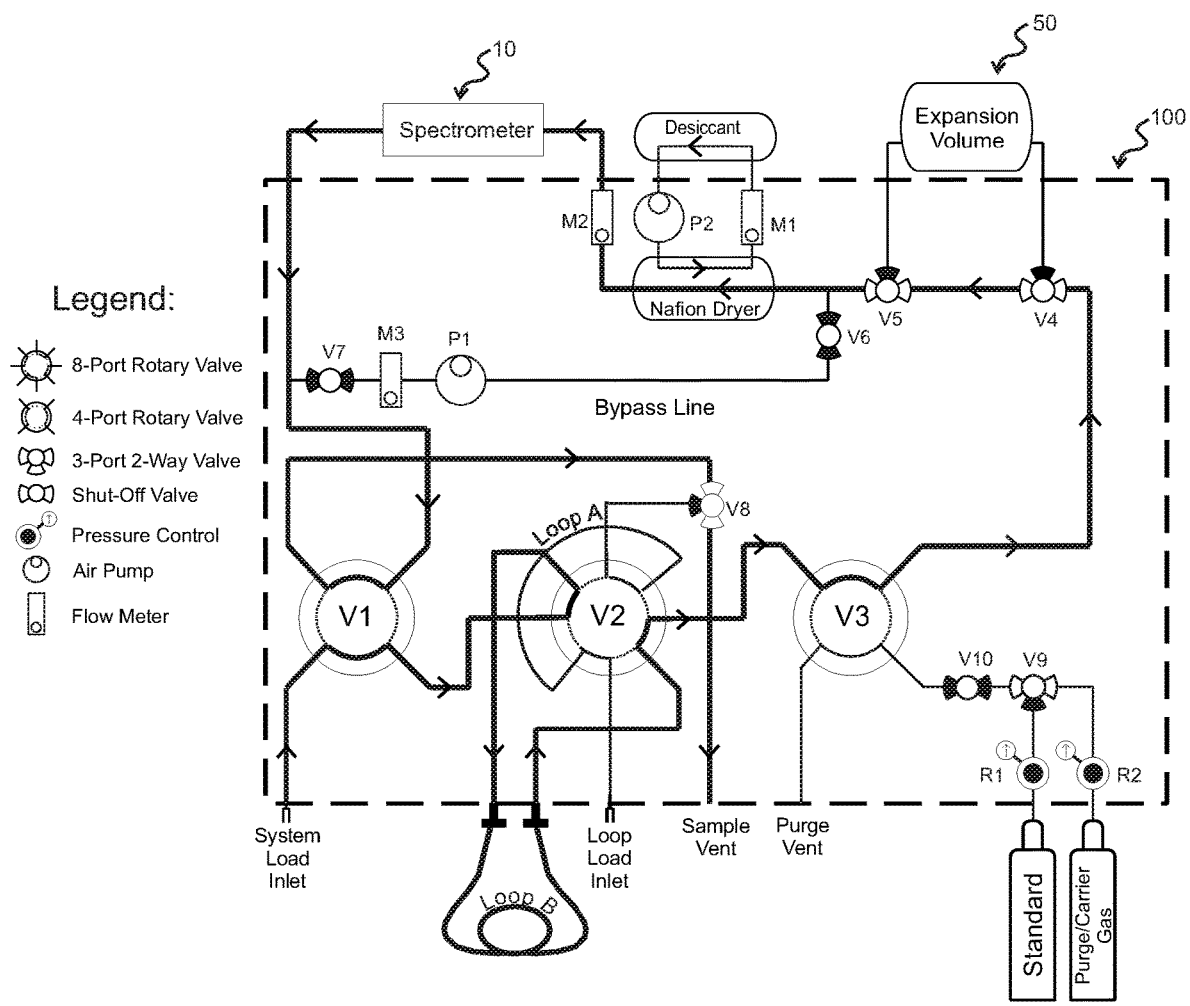
FIG. 5 illustrates an exemplary DSIM system configuration for a Load operation for a sample that does not require dilution.

FIG. 5 illustrates an exemplary configuration for System Load operation for a sample that does not require dilution. In the exemplary System Load process illustrated, the gas sample is introduced into the DSIM through the System Load Inlet. Samples with volumes enough to completely fill the analytical path are analyzed without dilution. The flow path for System Load is depicted by the solid, thick line.

Figure 6:
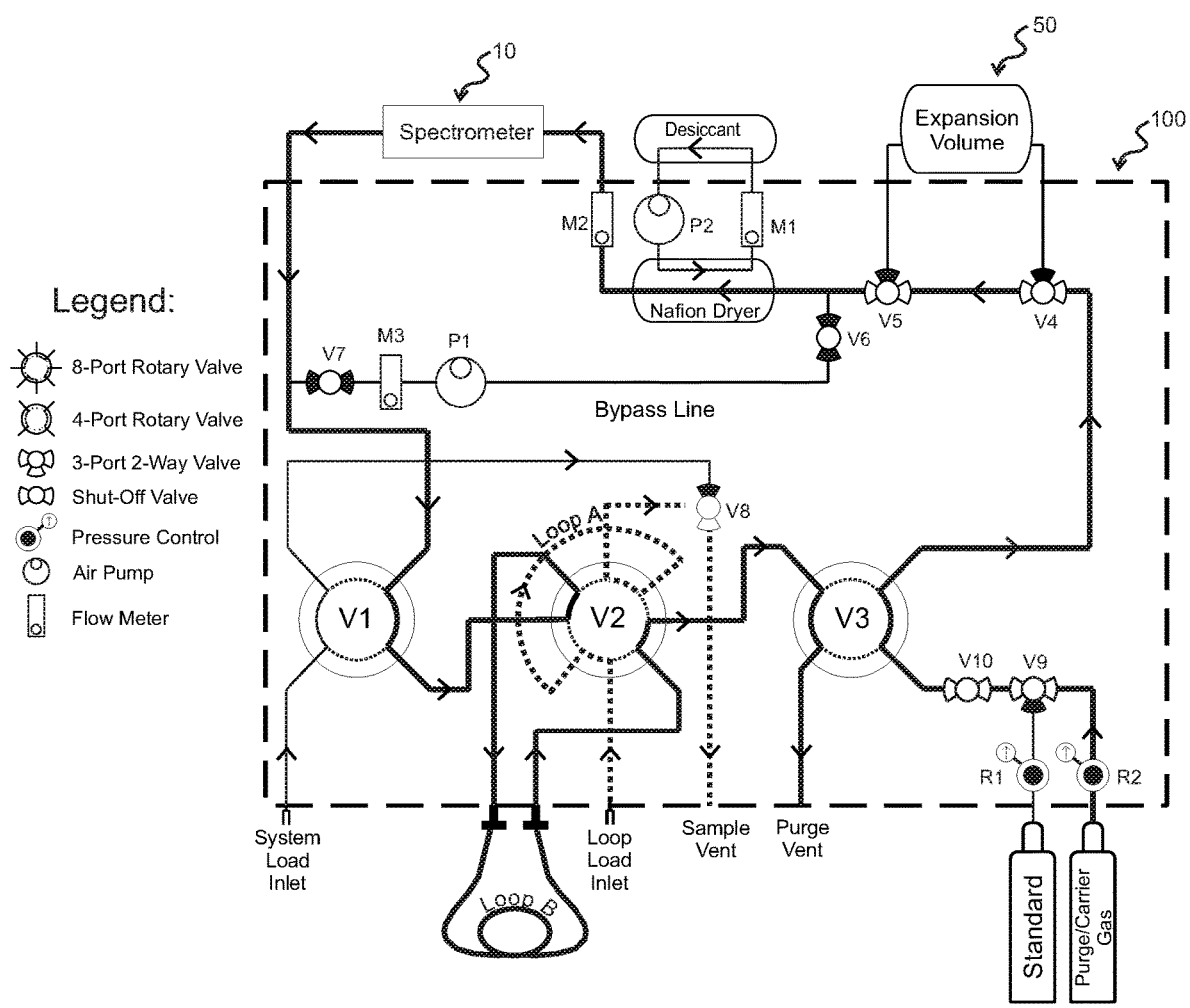
FIG. 6 illustrates an exemplary DSIM system configuration for performing a Load operation for performing a high level of dilution using the interior Loop A Load process.

FIG. 6 illustrates an exemplary DSIM system configuration for performing a Load operation when performing a high level of dilution using interior Loop A Load process. The discrete gas sample is introduced through the Loop Load Inlet, fills Loop A and is expelled through the Sample Vent (dashed line). Meanwhile, purge gas flushes the analytical path (solid, thick arrowed line).

In the exemplary embodiment shown, Loop A is an internal low-volume tubing section (~0.1 ml volume) that is attached to valve 2 (V2).

Figure 7:
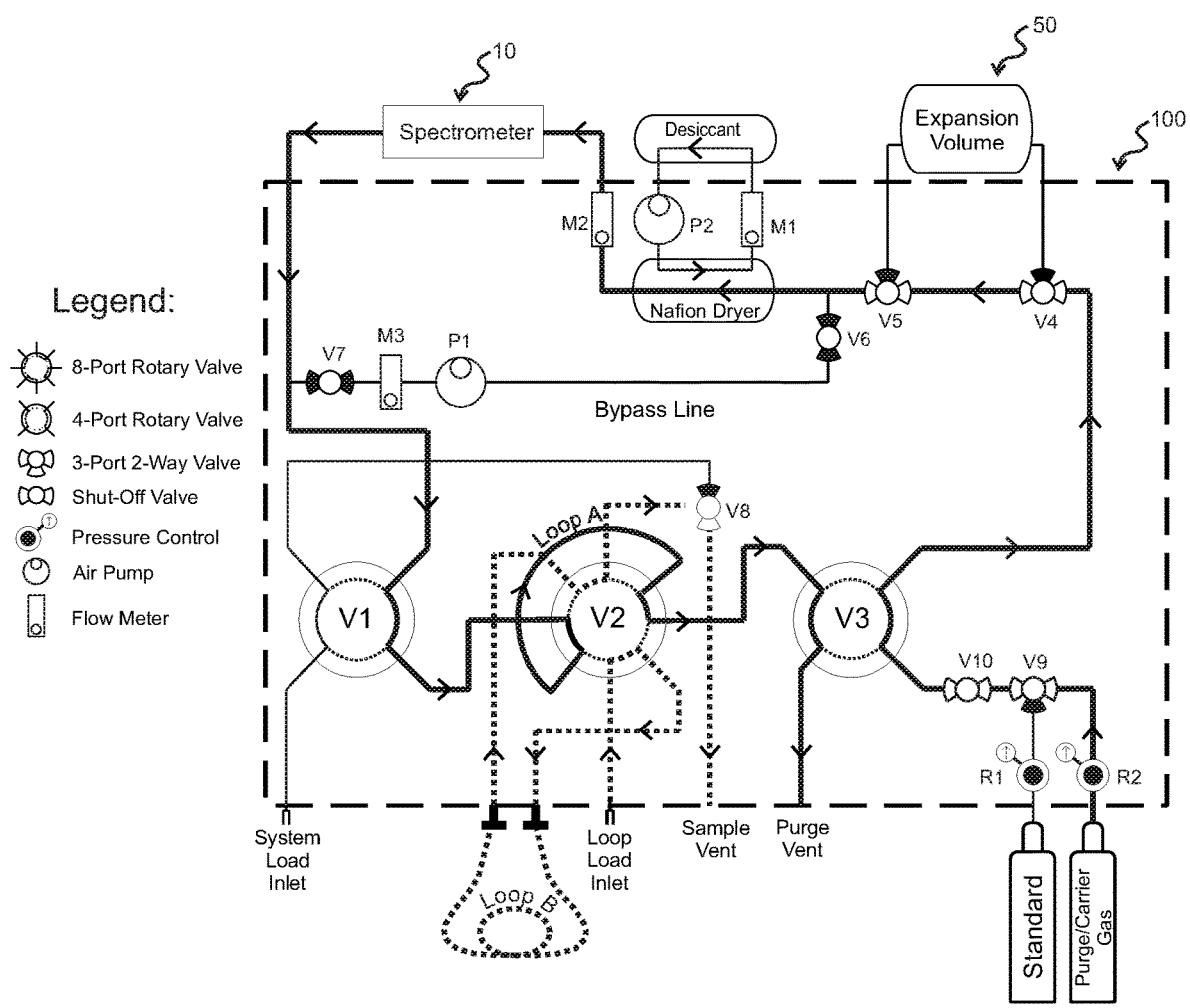
FIG. 7 illustrates an exemplary DSIM system configuration performing a Load operation using an external loop to accomplish an intermediate level of dilution.

FIG. 7 illustrates an exemplary DSIM system configuration performing a Load operation using an external loop to accomplish an intermediate level of dilution. In this exemplary embodiment, the discrete gas sample is introduced through the Loop Load Inlet, fills Loop B and is expelled through the Sample Vent (dashed line). Meanwhile, purge gas flushes the analytical path (thick line).

In the exemplary embodiment shown, the external Loop B is a higher-volume loop attached to the exterior of DSIM by compression fittings. The volume of Loop B can be determined by the user (usually 1-10 ml) or can be determined by the DSIM, e.g., based on inputs including a type of gas sample such as methane or carbon dioxide, and the range of dilution desired. Interior tubing connects the exterior component of Loop B to valve V2.

In another embodiment, the DSIM allows for the use of an incubation chamber to be connected as an external loop. The incubation chamber can be loaded with a sample, such as soil bacteria that decomposes a soil sample and respires a gas, e.g., carbon dioxide. The gases in the incubation chamber accumulate or change over time based on the incubation of the samples. The DSIM circulates these gases from the external loop incubation chamber and through the loop system analyzer, to measure how the concentration of the gases are changing over time due to the incubation being conducted in the incubation chamber over time.

Figure 8:
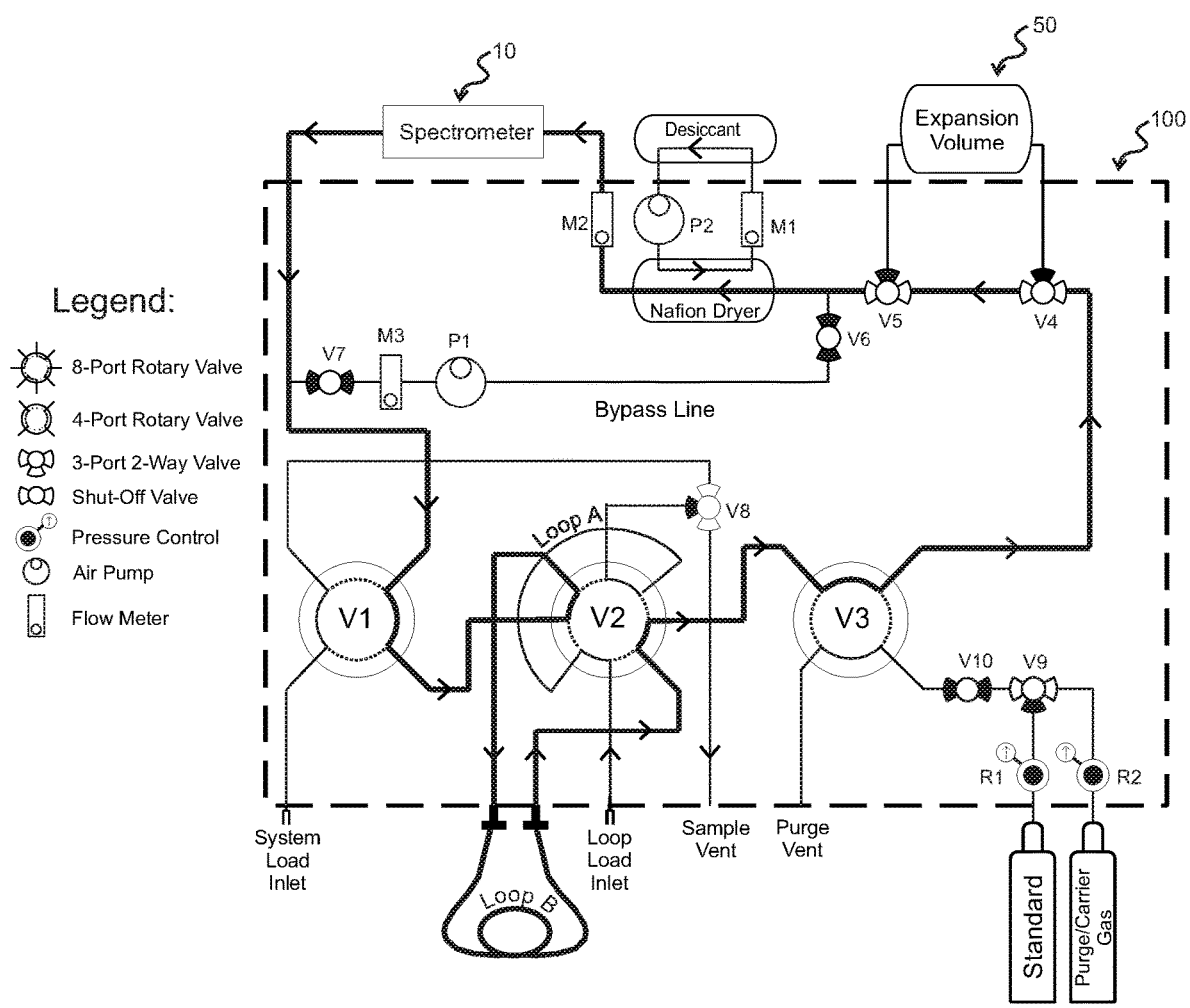
FIG. 8 illustrates an exemplary DSIM system analysis process for a sample that does not require dilution.

FIG. 8 illustrates an exemplary DSIM system analysis process for a sample that does not require dilution. In the exemplary embodiment shown, the gas sample introduced during System Load is recirculated within the analytical path without dilution. The analytical path is depicted by the thick line.

Figure 9:
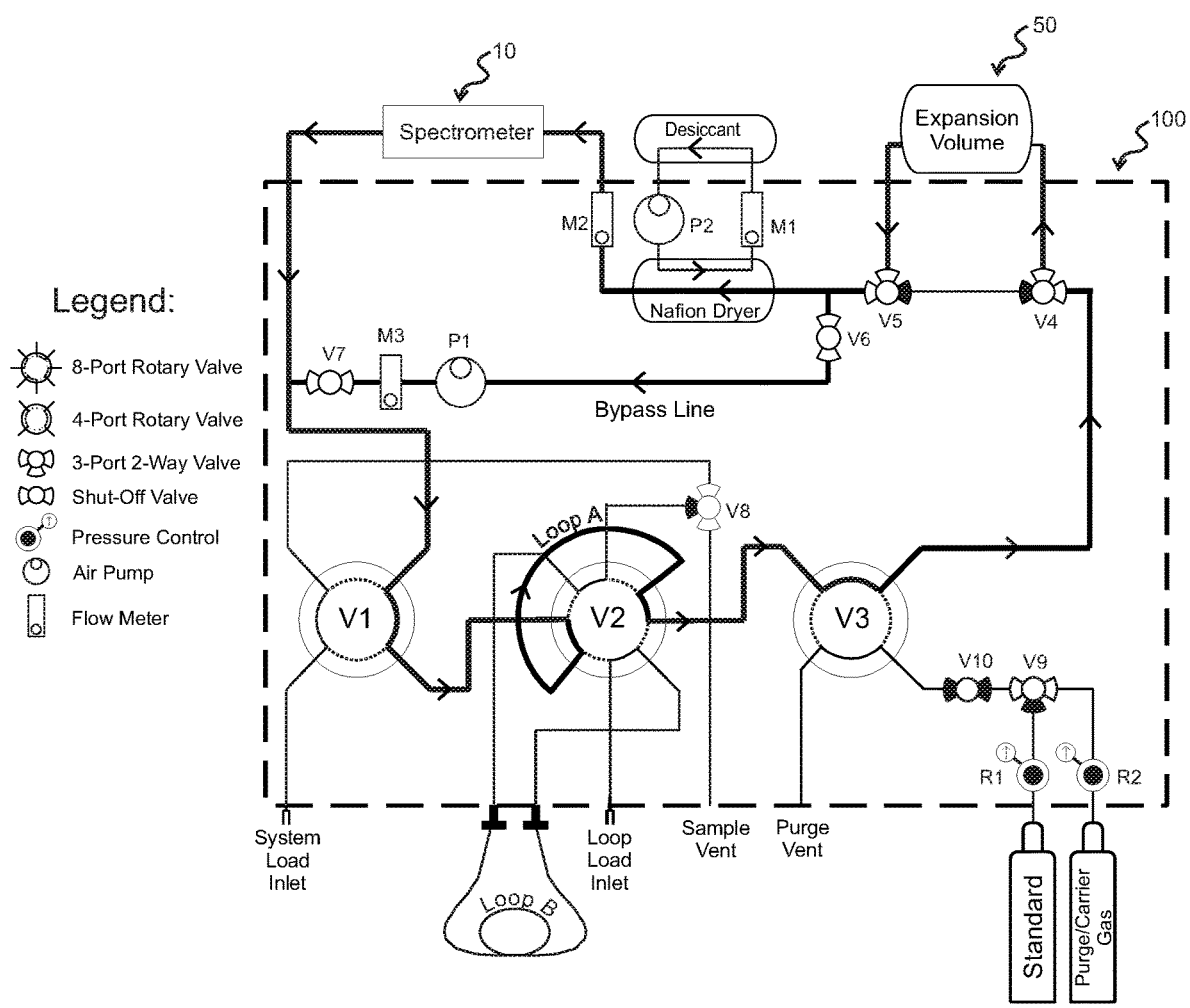
FIG. 9 illustrates an exemplary DSIM Loop Analysis process which utilizes an Expansion Component to increase system volume.

FIG. 9 illustrates an exemplary DSIM Loop Analysis process following Loop A Load process which utilizes an Expansion Component to increase system volume. The gas sample introduced during Loop A Load is recirculated and diluted within the analytical path. The Bypass Line facilitates mixing. When maximum dilution is required, the Expansion Volume is incorporated into the analytical path. The analytical path with the Expansion Volume enabled is depicted by the thick line.

Figure 10:
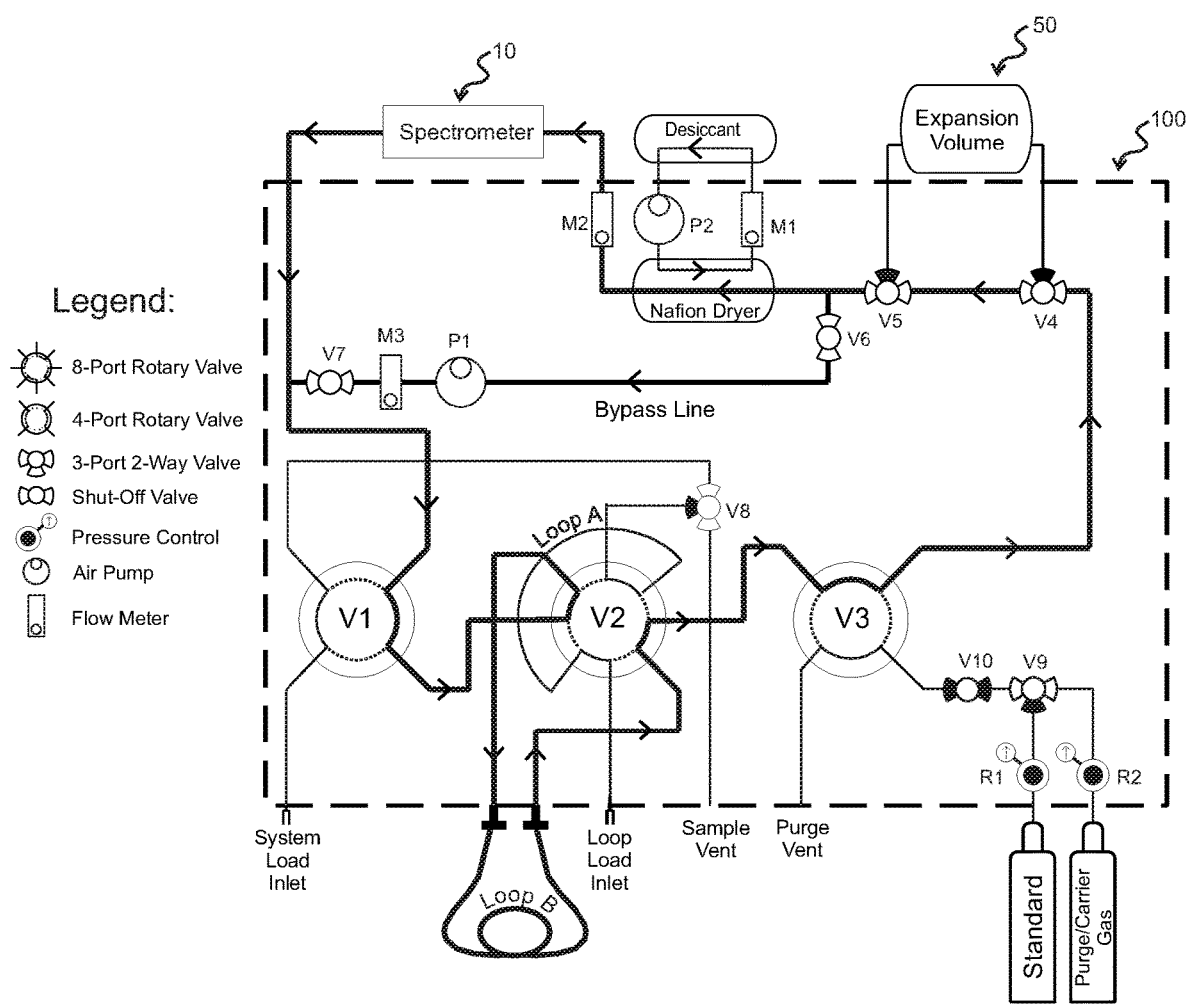
FIG. 10 illustrates an exemplary analysis process for a sample having an intermediate level of dilution.

FIG. 10 illustrates an exemplary analysis process for a sample having an intermediate level of dilution. In the exemplary embodiment shown, gas sample introduced during Loop B Load is recirculated and diluted within the analytical path. The Bypass Line facilitates mixing. The analytical path is depicted by the thick line.

The Expansion Volume is not typically employed during Loop B Dilution Analysis, because Loop A Dilution Analysis without the Expansion Volume provides comparable dilution, uses less sample, and is more easily purged following analysis. Sample results are corrected to account for dilution factors specific to each dilution analysis configuration. For example, the specific volume of a given dilution analysis configuration is known for a given DSIM, and that volume is used to adjust or correct the dilution factor used.

The rate of recirculation and therefore mixing within DSIM is increased through activation of the Bypass Line. The air pump (P1) of the Bypass Line increases the linear velocity of gas flowing within DSIM except for the gas going to the spectrometer 10, also referred to as Gas Analyzer. The Gas Analyzer's pump determines the linear velocity of gas passing through the drying system and Gas Analyzer. After passing through the Gas Analyzer, the sample gas converges with gas flowing through the Bypass Line. Sample results are obtained when a stable measurement signal indicates the sample and carrier gas are completely mixed.

In an embodiment, the DSIM generates the stable measurement signal by using an algorithm incorporating results of sample analyses. The DSIM determines incremental changes in sample values of a gas sample as it passes around the internal loop while mixing and being analyzed by the spectrometer 10. As the sample mixes and circulates, the sample values change by less and less. The DSIM applies equations to process the signal in the sample value changes, to determine whether the sample value changes have sufficiently dampened or flattened out over time. The DSIM identifies at what point the variation in the sample value change signal reaches an acceptable threshold (e.g., reaching a sample noise floor of the spectrometer 10), indicating that the gases are completely mixed and the DSIM is to generate the stable measurement signal. The DSIM determines various different lengths of time corresponding to generating the stable measurement signal for given types of gas samples, volumes, or other combinations of characteristics. The DSIM can request input on the type of sample gas, desired dilution, loop volume, and other features/parameters before beginning analysis, to predetermine an appropriate length of time for generating the stable measurement signal for the analysis to be carried out with the given parameters.

Figure 11:
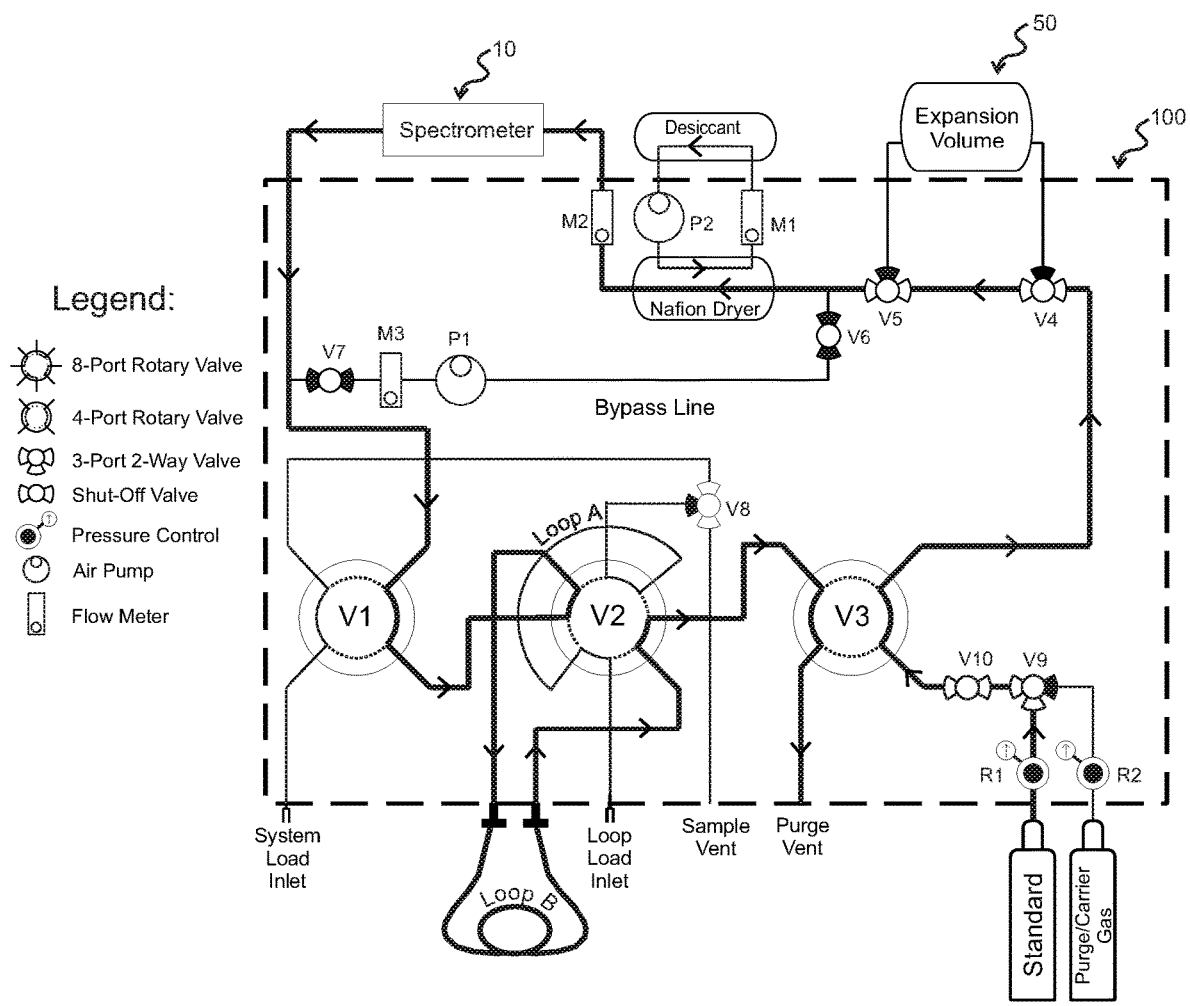
FIG. 11 illustrates an DSIM system calibration and monitoring process using Standard Gas.

FIG. 11 illustrates a DSIM system calibration and monitoring process. In the exemplary embodiment shown, a gas standard is delivered directly to the analyzer for instrument calibration and for monitoring instrument performance. The analytical path for the standard gas is depicted by the solid, thick, arrowed line. FIG. 11 also illustrates DSIM drying components. The Drying System preferably removes water vapor from gas in the analytical system during all operational modes. Water vapor is removed from the analytical line by, e.g., a sulfonated tetrafluoroethylene based fluoropolymer-copolymer tube (such as the a NAFION® dryer tube manufactured by Perma Pure LLC) and is captured by the drying gas and, in turn, trapped by a hydroscopic Desiccant attached to the exterior of DSIM. The drying system runs continuously in all embodiments of DSIM 100 as depicted in all figures.

Figure 12:
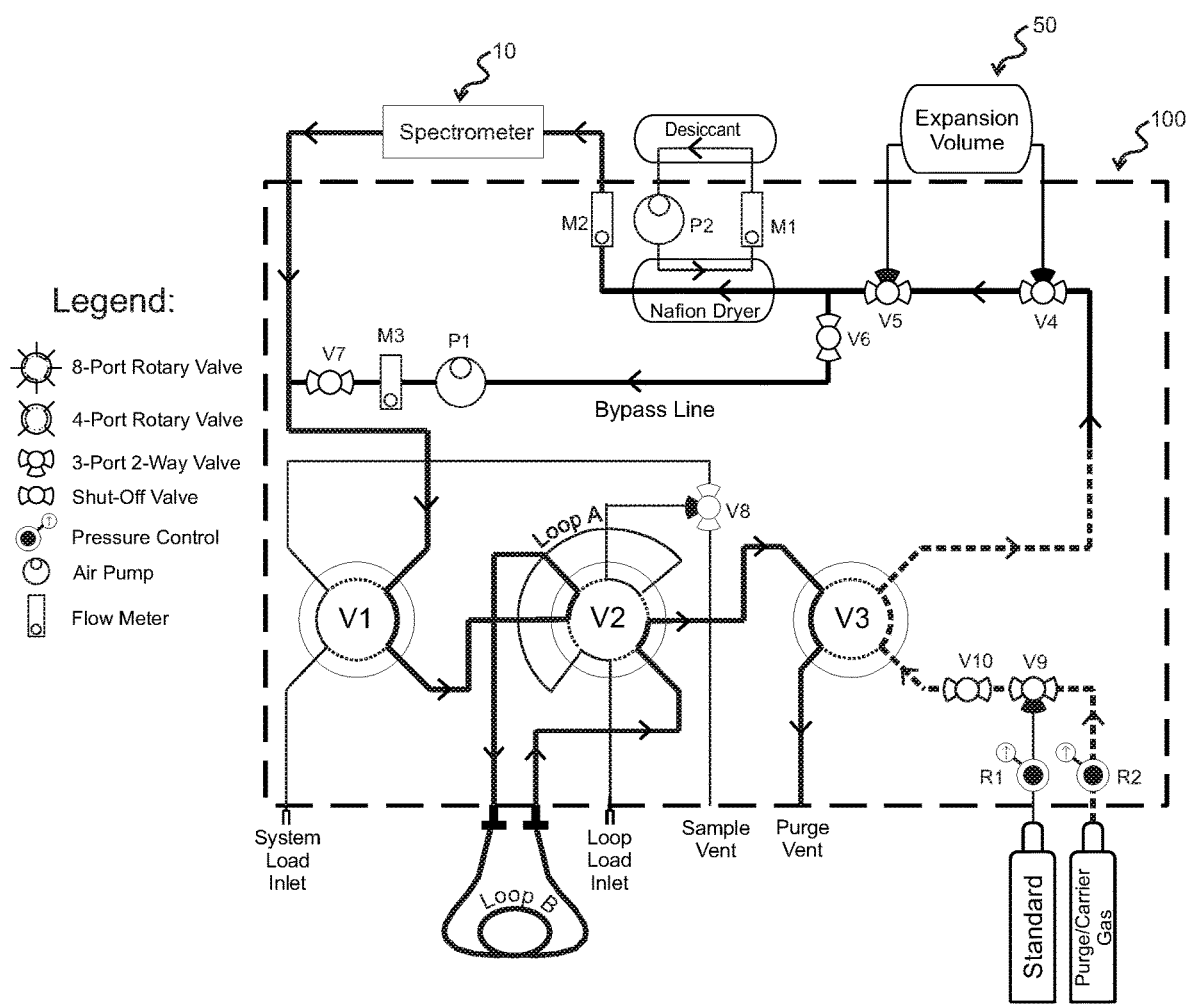
FIG. 12 illustrates an exemplary Stepdown Dilution process.

FIG. 12 illustrates an exemplary Stepdown Dilution process. The selective, incremental addition of Purge Gas into the analytical path (dashed line) replaces sample volume (thick line) in the analytical path. Repeated incremental dilutions are performed to achieve a specific concentration range, which is useful for gas isotope ratio measurements, which are accurate within a smaller operational range than absolute gas concentration measurements. Furthermore, the repeated incremental dilutions can be performed while checking results of the spectrometer 10, to determine at what point the dilution reaches a level that is compatible with the spectrometer 10 being capable of providing valid results. This technique enables the DSIM 100 to identify relative performances of different spectrometers 10, e.g., to tell with which given dilution a spectrometer 10 is compatible.

While the invention has been described and shown in terms of what are considered to be the most practical and preferred embodiments, it is understood that the invention covers various modifications, such as changes of types of gases to be tested, various changes in loop and system volumes and similar arrangements and use of equivalent components are included within the scope of this application's disclosure.

What is claimed is:

1. A Discrete Sample Introduction Module (DSIM) apparatus comprising:
   an internal tubing system to receive into the DSIM apparatus a discrete gas sample having a received concentration; and
   a plurality of valves to selectively partition the internal tubing system to form a plurality of loops each having a loop volume to contain the discrete gas sample;
   each of the loop volumes being configured to receive a carrier gas to dilute the discrete gas sample to a plurality of preselected dilutions, wherein
   the DSIM apparatus circulates a given one of the plurality of preselected dilutions for analysis by a spectrometer coupled to the DSIM apparatus.

2. The DSIM apparatus of claim 1, the internal tubing system is capable of forming part of a closed system loop including an analytical path such that the valves are opened and closed to circulate only the preselected dilutions through the system.

3. The DSIM apparatus of claim 2, wherein the internal tubing further comprises an expansion component to increase system volume suitable for analyzing the discrete gas sample.

4. The DSIM apparatus of claim 2, wherein the internal tubing system includes a bypass line to facilitate mixing.

5. The DSIM apparatus of claim 4, further comprising a plurality of pumps to circulate gas in the plurality of loops and mix gas using the bypass line, wherein a bypass line pump increases linear velocity of gas diverted from the spectrometer to flow through the bypass line, relative to gas not diverted from the spectrometer.

6. The DSIM apparatus of claim 5, further comprising a flow meter to verify pump performance.

7. The DSIM apparatus of claim 6, further comprising a pressure sensor to verify proper functioning of the DSIM.

8. The DSIM apparatus of claim 1, wherein the plurality of loops includes a sample loop.

9. The DSIM apparatus of claim 8, wherein the sample loop further comprises an external loop outside of and connected to the DSIM suitable for analyzing the discrete gas sample.

10. The DSIM apparatus of claim 1, wherein the plurality of loops includes an A loop corresponding to a first preselected dilution, and a B loop corresponding to a second preselected dilution.

11. The DSIM apparatus of claim 1, wherein tile plurality of valves comprises electrically actuated multi-port rotary valves.

12. The DSIM apparatus of claim 1, further comprising a purge vent selectively coupled to the plurality of loops to allow purging of gas from the DSIM apparatus.

13. The DSIM apparatus of claim 1, further comprising at least one system load inlet configured to receive the discrete gas sample into the DSIM for analysis at an actual sample concentration without dilution.

14. The DSIM apparatus of claim 13, further comprising at least one loop load inlet configured to receive the discrete gas sample into a given one of the plurality of loops for analysis according to the given one of the plurality of preselected dilutions.

15. The DSIM apparatus of claim 1, wherein the plurality of preselected dilutions include an internal dilution factor corresponding to an internal volume, an external dilution factor corresponding to dilution contribution by an external volume, and an expansion dilution factor corresponding to dilution contribution by an expansion volume.

16. The DSIM apparatus of claim 1, wherein the plurality of preselected dilutions are preselected for analysis of a preselected type of gas, and include a non-dilution factor, a dilution factor of 100, a dilution factor of 800, and a dilution factor of 1500.

17. The DSIM apparatus of claim 1, wherein the plurality of preselected dilutions overlap with each other to enable the DSIM apparatus to achieve a continuous spectrum of preselected dilutions ranging from non-dilution to a highest preselected dilution.

18. The DSIM apparatus of claim 1, further comprising an external coupling to interface each of the loop volumes with one of a plurality of external loops, wherein the plurality of external loops are associated with a respective plurality of external loop volumes corresponding to the plurality of preselected dilutions.

19. The DSIM apparatus of claim 18, wherein the plurality of external loop volumes includes a 1 ml volume corresponding to performing methane analysis, and a 5 ml volume corresponding to performing carbon dioxide analysis.

20. The DSIM apparatus of claim 18, wherein the external coupling is configured to interface with an incubation chamber, to allow the DSIM apparatus to monitor changes in gases caused by the incubation chamber over time.

21. The DSIM apparatus of claim 2, further comprising a closed gas drying system forming part of the closed system loop and configured to extract water across a membrane that isolates the discrete gas sample from the closed gas drying system while enabling gas circulation.

22. A method to dilute a discrete gas sample for analysis by a spectrometer, comprising:
   selectively partitioning, using a plurality of valves, an internal tubing system to form a plurality of loops each having a loop volume;
   receiving, into a given one of the plurality of loops, a discrete gas sample having a received concentration;
   receiving, into the given one of the plurality of loops, a carrier gas to dilute the discrete gas sample to a given preselected dilution corresponding to the given one of the plurality of loops;
   and circulating the given preselected dilution for analysis by the spectrometer.

23. The method of claim 22, wherein the given one of the plurality of loops in which the discrete gas sample is received is a sample loop selectively isolated from the given one of the plurality of loops by one or more valves, the method further comprising:
   actuating the one or more valves to couple the sample loop with the given one of the plurality of loops, to combine the discrete gas sample and
   the carrier gas, diluting the discrete gas sample to the given preselected dilution.

24. The method of claim 22, further comprising incrementally adding a purge gas into an analytical path of the given one of the plurality of loops to perform stepdown dilution by progressively further diluting the discrete gas sample.

25. The method of claim 24, further comprising:
   performing the stepdown dilution to bring into dilution range of the spectrometer a component of the discrete gas sample;
   determining the component dilution so reached;
   repeating the stepdown dilution to bring into dilution range of the spectrometer a next component of the discrete gas sample; and
   determining the next component dilution so reached.

26. The method of claim 22, further comprising:
   diverting at least a portion of gas flow from the spectrometer to a bypass line by opening a first shut-off valve and a second shut off valve and powering an air pump associated with the bypass line; and
   recombining, downstream of the spectrometer, diverted gas flow of the bypass line with spectrometer gas flow, to maintain continuous recirculation in the given one of the plurality of loops.

27. The method of claim 26, further comprising:
   determining that sufficient bypass line mixing time has passed; and
   generating a stable measurement signal, indicating that gases are sufficiently mixed and ready for analysis by the spectrometer.

28. The method of claim 22, further comprising:
   coupling an incubation chamber with the given one of the plurality of loops; and
   determining gas levels from the incubation chamber over time while incubating.

* * * * *